(12) United States Patent
Joanis et al.

(10) Patent No.: US 9,372,191 B2
(45) Date of Patent: Jun. 21, 2016

(54) **METHODS AND DEVICES FOR DETECTING METHICILLIN RESISTANT *STAPHYLOCOCCUS AUREUS***

(75) Inventors: Dorothy Joanis, Hollis Center, ME (US); Myron Whipkey, Auburn, ME (US); Erin Hayes, Lewiston, ME (US); Steven Muszynski, Biddeford, ME (US); Alan H. Davis, Falmouth, ME (US); Kristin Gordon, Scarborough, ME (US); Roger N. Piasio, Cumberland Foreside, ME (US); Norman James Moore, North Berwick, ME (US)

(73) Assignee: Alere Switzerland GmbH, Zug (CH)

( * ) Notice: Subject to any disclaimer, the term of this patent is extended or adjusted under 35 U.S.C. 154(b) by 1041 days.

(21) Appl. No.: 12/517,771

(22) PCT Filed: Dec. 10, 2007

(86) PCT No.: PCT/US2007/086985
§ 371 (c)(1),
(2), (4) Date: May 4, 2010

(87) PCT Pub. No.: WO2008/140608
PCT Pub. Date: Nov. 20, 2008

(65) Prior Publication Data
US 2010/0304414 A1 Dec. 2, 2010

Related U.S. Application Data

(60) Provisional application No. 60/873,865, filed on Dec. 8, 2006.

(51) Int. Cl.
*G01N 33/53* (2006.01)
*C12Q 1/18* (2006.01)
*G01N 33/569* (2006.01)

(52) U.S. Cl.
CPC .............................. *G01N 33/56944* (2013.01)

(58) Field of Classification Search
USPC ..................... 435/7.1, 7.2, 7.3, 7.4, 32, 353
See application file for complete search history.

(56) References Cited

U.S. PATENT DOCUMENTS

2005/0250141 A1* 11/2005 Lambert et al. .................. 435/6
2006/0051820 A1* 3/2006 Horii et al. ................... 435/7.32

OTHER PUBLICATIONS

Nakatomi et al (Microbiology and Immunology. 1998. 42: 739-742).*
Wolz, C. et al. (Infectious Immunity. 1996. 64(8): 3142-3147).*
Huang et al (Clinical Chemistry Sep. 2004 vol. 50 No. 9 1673-1674).*
Nakatomi, Y. "A Rapid latex agglutination assay for the detection of penicillin-binding protein 2," Microbiology and Immunology 42: 739-743 (1998) (Abstract).
Wolz, C., et al. "Influence of agr on fibrinogen binding in *Staphylococcus aureus* Newman," Infectious Immunity 64(8): 3142-3147 (1996).
International Search Report and Written Opinion for PCT/US2007/086985 dated Nov. 3, 2008.

* cited by examiner

*Primary Examiner* — Jennifer Graser
(74) *Attorney, Agent, or Firm* — Foley Hoag LLP

(57) ABSTRACT

Provided are methods and devices for detecting methicillin-resistant *Staphylcoccus aureus*.

4 Claims, 4 Drawing Sheets

Positive (+):

A positive test result will include the detection of both a Test and a Control Line.

Negative (-):

A negative test result, will produce only a Control Line, indicating that the pathogen was not detected and the test worked properly.

If a control line does not appear, the assay is INVALID.

METHODS AND DEVICES FOR DETECTING METHICILLIN RESISTANT *STAPHYLOCOCCUS AUREUS*

RELATED APPLICATIONS

This application is a 371 national stage application of PCT/US2007/086985, filed Dec. 10, 2007, which claims priority to U.S. Provisional Application No. 60/873,865, filed Dec. 8, 2006.

BACKGROUND

Methicillin-resistant *Staphylococcus aureus* (MRSA) is a bacterium resistant to the antibiotic methicillin. *Staphylococcus aureus*, sometimes referred to simply as "staph," or "staph A" is a common bacterium found on the skin of healthy people. If staph gets into the body it can cause a minor infection such as boils or pimples or serious infections such as pneumonia or blood infections.

One antibiotic commonly used to treat staph infections is methicillin. While methicillin is very effective in treating most staph infections, some staph bacteria have developed a resistance to methicillin and can no longer be killed by this antibiotic. The resistant bacteria are called methicillin-resistant *staphylococcus aureus* or MRSA.

Current methods for the detection of staph and MRSA may not be performed directly from blood culture bottles. In the methods, a sample is taken from a positive blood culture bottle and plated onto culture medium and grown overnight. A colony is removed from the culture medium and its species determined by a coagulase test. If it is coagulase-positive, the organism is staph A, if it is coagulase-negative, it is another species of *Staphylococcus*. Once the organism is determined to be staph A, a colony is plated onto culture medium containing methicillin and grown for a minimum of 24 hours. If the organism grows, it is MRSA and if it does not grow, it is methicillin-sensitive *Staphylococcus aureus* (MSSA). Thus, such methods are time-consuming and involve many steps, including preparing a secondary culture plate.

SUMMARY

Provided are methods and devices to determine the presence of MRSA directly in positive blood cultures. The methods comprise analyzing blood specimens taken directly from positive blood culture bottles using two immunoassays to determine if the sample is MRSA. The first immunoassay detects the presence of the particular gram positive bacteria (e.g. *Staphylococcus* A). The second assay detects a drug resistance (e.g. methicillin-resistant (positive result) or methicillin-sensitive (negative result)).

Use of the two immunoassays provides a significant time advantage and simplicity over conventional methods. Conventional methods take up to 48 hours after the blood culture bottle has signaled positive on the instrument to determine if the organism is MRSA. Using the two immunoassays requires a maximum of four (4) hours once the blood culture bottle signals positive.

Further objectives and advantages of the present invention will become apparent as the description proceeds. To gain a full appreciation of the scope of the present invention, it will be further recognized that various aspects of the present invention can be combined to make desirable embodiments of the invention.

DETAILED DESCRIPTION

Figure 1:
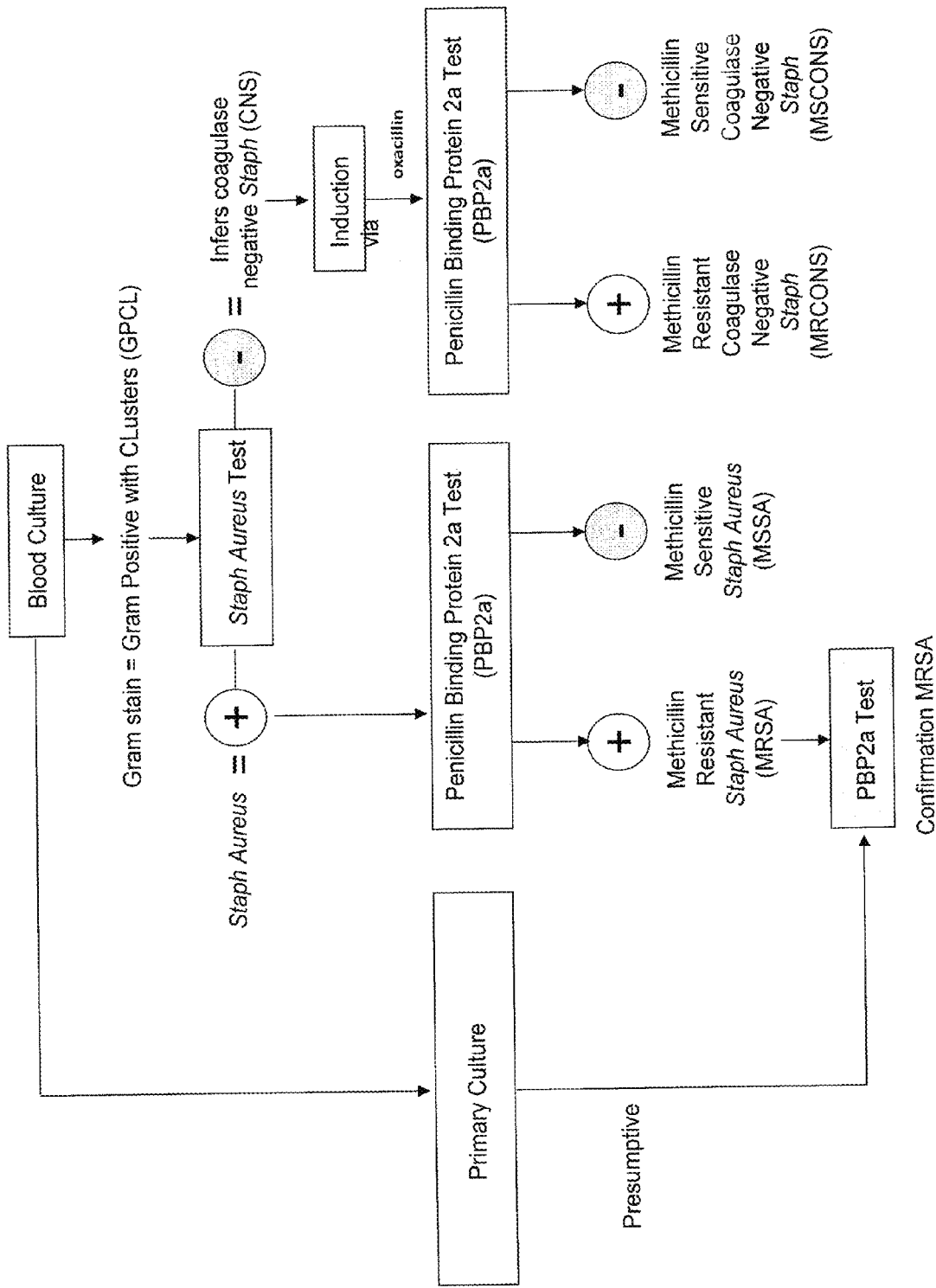
FIG. 1 depicts a schematic of the provided methods for determining if the bacteria in a sample are MRSA, MSSA or another species of staph.

Unless defined otherwise above, all technical and scientific terms used herein have the same meaning as commonly understood by one of ordinary skill in the art to which this invention belongs. Where a term is provided in the singular, the inventor also contemplates the plural of that term. The nomenclature used herein and the procedures described below are those well known and commonly employed in the art.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In exemplary embodiments, antibodies used with the methods and compositions described herein are derivatives of the IgG class.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The terms "comprise" and "comprising" is used in the inclusive, open sense, meaning that additional elements may be included.

The term "including" is used herein to mean "including but not limited to". "Including" and "including but not limited to" are used interchangeably.

The term "sample" refers to any sample potentially containing *Staphylococcus* bacteria. For example, a sample may be a bodily fluid such as blood, urine or saliva.

Provided are methods and devices for determining whether a bacterium in a blood sample is an antibiotic-resistant bacterium, wherein the determining is performed by analyzing blood specimens taken directly from positive blood culture bottles. In certain embodiments, the methods and devices are for determining whether a bacterium in a blood sample is methicillin-resistant staph A.

In certain embodiments, the methods comprise analyzing blood specimens taken directly from positive blood culture bottles using two lateral flow devices to determine if the sample is MRSA.

In certain embodiments, the methods may comprise: (a) detecting, using a first immunoassay, which detects specific gram positive bacteria in a sample from a gram positive blood culture; and (b) determining, in the sample from the gram positive blood culture via a second immunoassay, whether the detected species of gram positive bacteria is resistant to a particular antibiotic.

In certain embodiments, the detected species of gram positive bacteria is a *Staphylococcus* species. The species may be detected by using a first immunoassay that detects an enzyme or other protein present on a particular species of gram positive bacteria, i.e., an enzyme or other protein or molecule unique to that particular species. In certain embodiments, the enzyme is coagulase.

Whether the species is resistant to a particular antibiotic or not may be determined by a immunoassay. In certain embodiments, the assay is for a protein produced by a species of gram positive bacteria resistant to a particular antibiotic. In certain embodiments, the marker for antibiotic resistance is a penicillin binding protein and the antibiotic is methicillin.

The immunoassays may comprise antibodies to detect the enzyme or other protein present on a particular species of gram positive bacteria, or the protein produced by a species of gram positive bacteria resistant to a particular antibiotic.

In certain embodiments, the method may comprise the steps of: (a) detecting, using a first immunoassay, whether *Staphylococcus aureus* or another species of *Staphylococcus* is present in a sample from a gram positive blood culture; and (b) determining, in the sample from the gram positive blood culture via a second immunoassay, whether the detected species of *Staphylococcus* is methicillin resistant. In certain embodiments, the methods may further comprise a preliminary step of obtaining a sample from a gram positive blood culture.

FIG. 1 depicts a schematic of the order in which such methods may be used to determine the bacteria in a sample are MRSA, MSSA or another species of staph.

The steps in the methods described above may be accomplished by any immunoassay format, including lateral flow, ELISA and direct fluorescence assays. In some embodiments, the species detection step may be performed with one type of assay or device and the antibiotic resistance detection step may be performed with another type of assay or device.

For use in the methods described above, kits and devices for the practice of the above-described methods are also provided. Devices for practice of the methods include lateral flow devices (wherein the reagents employed in the reaction may be dried or immobilized onto a chromatographic support contained within the device), a test strip, or other support for practice of the methods. A kit for the practice of the above methods may include a support, reagents and wash and incubation buffers. Such kits and devices can contain any number or combination of reagents or components. The kits can comprise one or more of the above components in any number of separate containers, tubes, vials and the like or such components can be combined in various combinations in such containers. Kit components may be packaged for either manual or partially or wholly automated practice of the foregoing methods. Further, instructions for the use of a device or kit may be included with the device or kit. Such kits and devices may have a variety of uses, including, for example, diagnosis, therapy, and other applications.

EXEMPLIFICATION

The invention, having been generally described, may be more readily understood by reference to the following examples, which are included merely for purposes of illustration of certain aspects and embodiments of the present invention, and are not intended to limit the invention in any way. All headings are for the convenience of the reader and should not be used to limit the meaning of the text that follows the heading, unless so specified.

Example 1

Exemplary MRSA Test Procedures Using a Prototype Device

Figure 2:
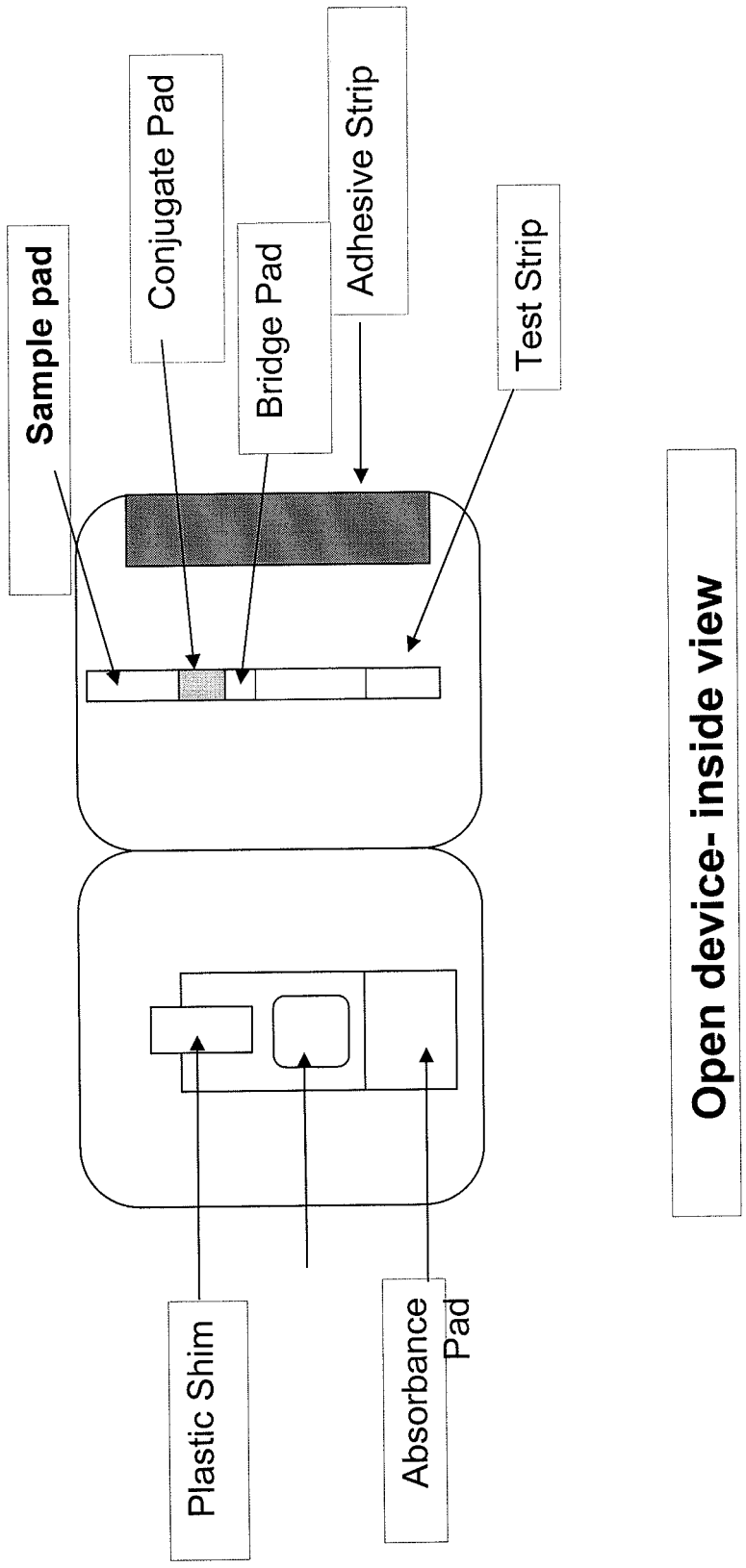
FIG. 2 depicts a prototype device which may in some embodiments be used to implement the provided methods. Antibodies or other molecules able to bind to molecules specific to an antigen, for example, staph A antigens or penicillin-binding protein 2a are conjugated to a test zone on the conjugate pad. A control zone is also present on the conjugate pad.

In one embodiment, the methods comprise assaying for staph A first as a screen and then assaying for penicillin-binding protein 2a using two lateral flow devices. A device as shown in FIG. 2 may be used to implement the lateral flow devices as follows:

A. Staph A Test Procedure
1. Aspirate the sample directly from a positive blood culture bottle, via syringe.
2. Centrifuge the sample for 10 minutes at 10,000×g.
3. Slowly dispense 100 uL of the supernatant sample directly onto the sample pad of the device.
4. Allow the sample to flow to the bottom of the test strip.
5. Peel off the brown adhesive strip and close the device.
6. Read the result within 15-30 minutes after closing the device. If the sample is positive, proceed to the PBP2a assay.

B. PBP2α Test Procedure (#1)
1. Aspirate sample from a blood culture bottle, via syringe, if the sample tests positive on the staph A assay.
2. Centrifuge the sample for 5 minutes at 3,000 rpm.
3. Remove 1.0 mL of the supernatant. Add 100 uL of the extraction buffer and mix.
4. Slowly dispense 100 uL of the sample directly onto the sample pad of the device.
5. Allow the sample to flow to the bottom of the test strip.
6. Peel off the brown adhesive strip and close the device.
7. Read the result within 15-30 minutes after closing the device.

C. PBP2α Test Procedure (#2)
In this alternative procedure, the device has a wash pad in place of the plastic shim.
1. Aspirate sample from a blood culture bottle, via syringe, if the sample tests positive on the staph A assay.
2. Add 100 uL of the extraction buffer and mix.
3. Centrifuge the sample for 10 minutes at 10,000×g.
4. Slowly dispense 100 uL of the sample directly onto the sample pad of the device.
5. Allow the sample to flow to the bottom of the test strip.
6. Add 4 drops of wash buffer to the wash pad.
6. Peel off the brown adhesive strip and close the device.
7. Read the result within 15-30 minutes after closing the device.

Figure 3:
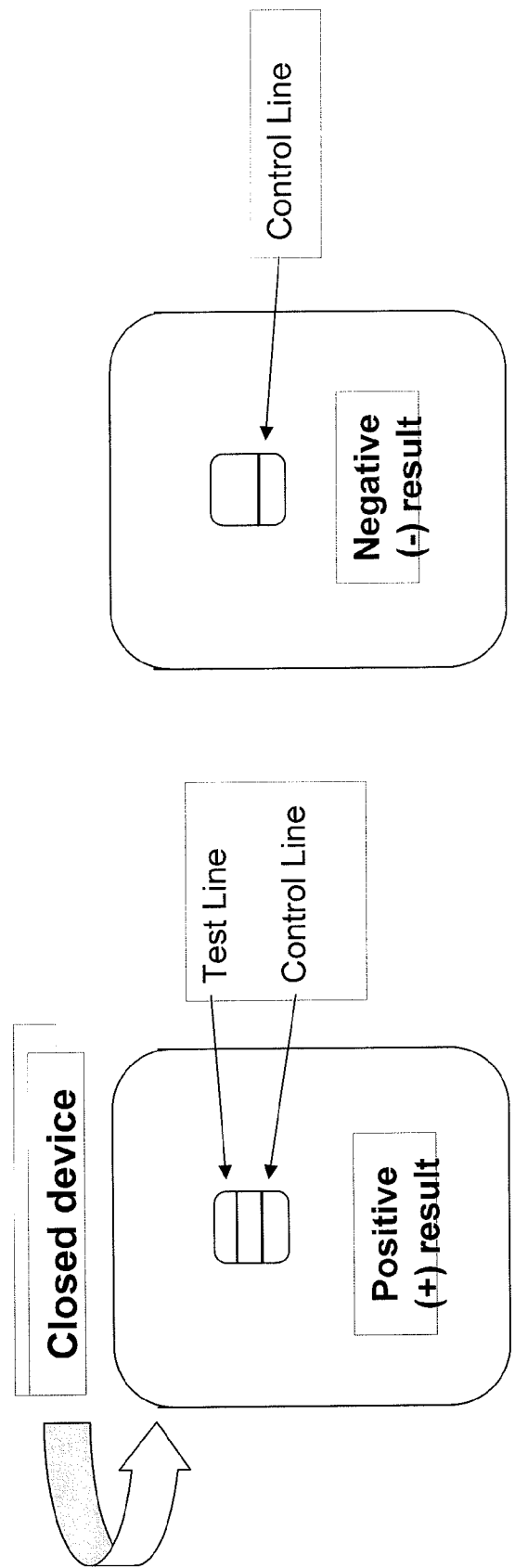
FIG. 3 depicts how to read positive or negative test results in the device of FIG. 2.
Figure 4:
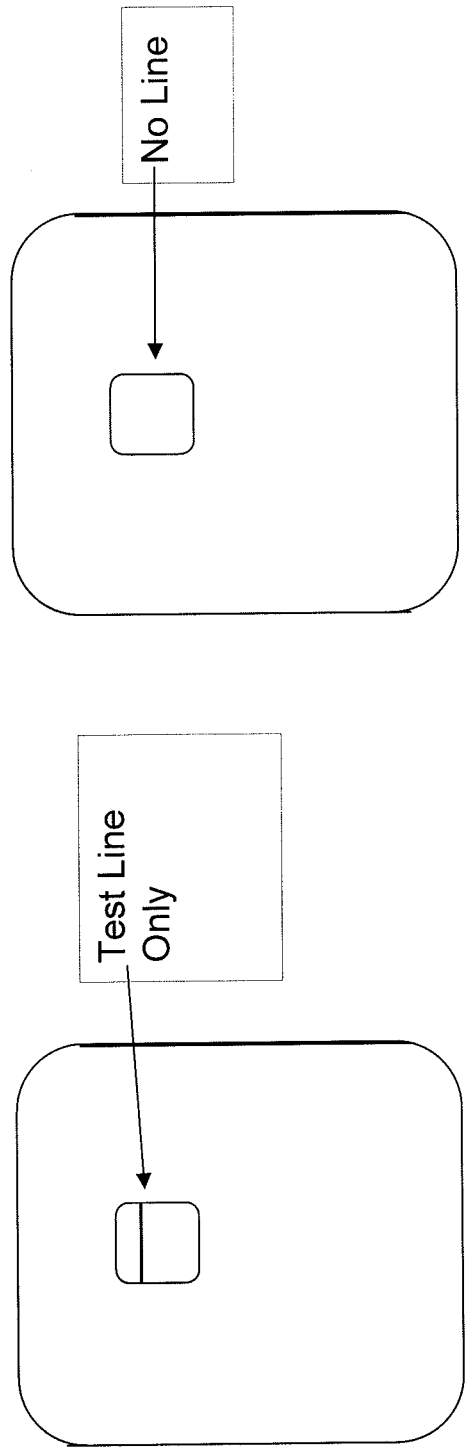
FIG. 4 depicts an invalid test result as read from the device of FIG. 2.

For any of the procedures, the test results may by read as indicated in FIG. 3 and FIG. 4.

EQUIVALENTS

Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations. Such equivalents are intended to be encompassed by the following claims.

We claim:

1. A method for determining the presence of antibiotic resistant *Staphylococcus aureus* in a gram positive blood culture sample, comprising the steps of:
    a. obtaining a sample from a gram positive blood culture, wherein the sample has not been further cultured,
    b. performing a first immunoassay comprising the steps of (i) contacting the sample with a sample pad to a first lateral flow device and (ii) visually detecting the presence of *Staphylococcus aureus* protein A in the sample using the first lateral flow device; and
    c. performing a second immunoassay comprising the steps of (i) contacting the sample with a sample pad to a second lateral flow device and (ii) visually detecting the presence of penicillin binding protein type A (PBP2A) in the sample using the second lateral flow device,
    wherein the presence of antibiotic resistant *Staphylococcus aureus* in the sample is determined, (i), if the result of the first immunoassay is positive for the detection of *Staphylococcus aureus* protein A and the result of the second immunoassay is positive for the detection of PBP2a, and (ii) in four hours or less from the time the sample is obtained from the gram positive blood culture.

2. The method of claim 1, wherein the antibiotic is methicillin.

3. The method of claim 1, wherein the result of the first immunoassay is read within 15-30 minutes of starting the assay.

4. The method of claim 1, wherein the result of the second immunoassay is read within 15-30 minutes of starting the assay.

* * * * *